United States Patent
Knas et al.

(10) Patent No.: US 10,650,922 B1
(45) Date of Patent: May 12, 2020

(54) INTERACTIVE MEAL-DATASET-BASED MAP

(71) Applicant: MASSACHUSETTS MUTUAL LIFE INSURANCE COMPANY, Springfield, MA (US)

(72) Inventors: Michal Knas, Monson, MA (US); Jiby John, Suffield, CT (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 0 days.

(21) Appl. No.: 16/357,055

(22) Filed: Mar. 18, 2019

Related U.S. Application Data

(63) Continuation of application No. 15/371,053, filed on Dec. 6, 2016, now Pat. No. 10,275,575.

(60) Provisional application No. 62/264,689, filed on Dec. 8, 2015.

(51) Int. Cl.
  *H04W 24/00* (2009.01)
  *G16H 20/60* (2018.01)

(52) U.S. Cl.
  CPC .................. *G16H 20/60* (2018.01)

(58) Field of Classification Search
  USPC ........ 455/456.1, 411, 566, 404.2; 705/14.58, 705/14.49
  See application file for complete search history.

(56) References Cited

U.S. PATENT DOCUMENTS

| | | | | |
|---|---|---|---|---|
| 6,954,735 | B1* | 10/2005 | Djupsjobacka | G06Q 30/06 701/533 |
| 7,356,357 | B2* | 4/2008 | DeCost | G06Q 20/327 455/566 |
| 2006/0161474 | A1 | 7/2006 | Diamond et al. | |
| 2009/0327135 | A1 | 12/2009 | Nguyen et al. | |
| 2010/0312793 | A1* | 12/2010 | Brown | G06F 16/338 707/770 |
| 2011/0112904 | A1* | 5/2011 | Stupp | G06Q 30/02 705/14.58 |
| 2012/0022944 | A1 | 1/2012 | Volpi | |
| 2013/0054695 | A1 | 2/2013 | Holman et al. | |
| 2013/0191211 | A1* | 7/2013 | Nichols | H04Q 67/18 705/14.49 |
| 2013/0290096 | A1 | 10/2013 | Lizotte, III | |

(Continued)

*Primary Examiner* — David Q Nguyen
(74) *Attorney, Agent, or Firm* — Eric L. Sophir; Foley & Lardner LLP

(57) ABSTRACT

A method to integrate location signals received from indoor positioning systems in order to generate an interactive dataset-based map is disclosed. The method comprises receiving an identifier and location information from a consumer device. The method comprises determining a current location for the consumer device based on the signal strength received from a beacon. The method comprises determining whether the identifier and the current location are associated with the consumer device in a database. The method comprises generating a set of meal datasets within a predetermined proximity to the consumer device. The method comprises generating a first graphical user interface to display the set of meals on the consumer device and receiving a selection of meals from the consumer device. The method comprises generating a second graphical user interface configured to display instructions to reach physical locations of the selected meal datasets in relation to the consumer device.

16 Claims, 6 Drawing Sheets

(56) References Cited

U.S. PATENT DOCUMENTS

| | | |
|---|---|---|
| 2014/0200911 A1 | 7/2014 | Schoenberg |
| 2014/0358835 A1* | 12/2014 | Marti ..................... G06N 5/02 |
| | | 706/46 |
| 2015/0079942 A1* | 3/2015 | Kostka ................... H04W 4/21 |
| | | 455/411 |
| 2015/0221316 A1 | 8/2015 | Mufti |
| 2016/0210954 A1 | 7/2016 | Takata et al. |
| 2016/0300285 A1* | 10/2016 | Gandhi ............. G06Q 30/0623 |
| 2017/0061101 A1 | 3/2017 | Hampden et al. |

\* cited by examiner

INTERACTIVE MEAL-DATASET-BASED MAP

CROSS-REFERENCE TO RELATED APPLICATION

This application is a continuation application of U.S. patent application Ser. No. 15/371,053, filed Dec. 6, 2019, which claims priority to U.S. Provisional Patent Application Ser. No. 62/264,689, filed Dec. 8, 2015, each of which is hereby incorporated by reference in its entirety.

FIELD OF DISCLOSURE

The present application relates generally to systems, methods, and other embodiments for managing meal datasets.

BACKGROUND

Increasingly, more and more consumers are conscious of the nutritional content of their food and beverages. Consumers are interested in more than basic numbers regarding calorific content, serving size, and amounts of carbohydrates, proteins, and fats. Even the most health-conscious and ingredient-aware consumer can be off target due to health framing issues, where companies present smaller serving sizes on nutrition labels than what a consumer actually eats, so that the nutrition label contains deceptively lower amounts of undesired components such as saturated fats and added sugars. Moreover, consumers want to know the sophisticated breakdown of content, such as how their food and beverage consumption breaks into the macronutrient and micronutrient categories, and how the ingredient content and cooking methods have impacted their nutrient consumption. Consumers are also interested in changing their food and beverage consumption to fit any one of the many diet plans such as the low-carbohydrate, or low-fat, or high-protein, or low-sugar diets, and how a healthy meal may or may not meet their dietary plan. However, analyzing all this data is not easy on a daily basis. Furthermore, in a social setting such as eating lunch with one's colleagues in a cafeteria or a food court, it is hard to acquire and understand the nutritional content for the food available in that setting. In many large cafeterias, it extremely difficult to plan, identify, and locate desired food, which complies with one's dietary restrictions.

SUMMARY

For the aforementioned reasons, there is a need to integrate indoor positioning systems for better management of meal options and facilitating consumers' desire to manage their dietary consumption for better health. The systems and methods disclosed herein attempt to address the above-mentioned shortcomings in the art and provide a variety of other benefits. The systems and methods described herein can create, maintain, transmit, and utilize data from consumer devices and beacons.

In an embodiment a method comprises receiving, by a server, a device identifier and location information from a consumer device, the location information being associated with a location of the consumer device and determined from a plurality of location signals received from a plurality of beacons, wherein the device identifier comprises a distinctive combination of at least one of numbers and characters uniquely identifying the consumer device. The method comprises determining, by the server, a current location associated with the consumer device based at least on one of the location information and strength of the location signal received from the plurality of beacons. The method comprises determining, by the server, whether the device identifier from the consumer device and the current location are associated with the consumer device in a database, wherein the database is configured to store a first plurality of records of a first plurality of meal dataset and one or more records of a plurality of consumer devices. The method comprises, in response to the device identifier and the current location being associated with the consumer device in the database, generating by the server, a second plurality of records associated to a second plurality of meal datasets in the database, the second plurality of meal datasets being selected from the first plurality of meal datasets based on availability within a predetermined proximity to the current location of the consumer device. The method comprises generating, by the server, a first graphical user interface configured to display the second plurality of meal datasets. The method comprises, upon transmitting the first graphical user interface to the consumer device, receiving by the server, one or more inputs corresponding to one or more selected meal datasets from the second plurality of meal datasets. The method comprises generating, by the server, a second graphical user interface configured to provide instructions to reach one or more physical locations of the one or more selected meal datasets in relation to the current location of the consumer device. The method comprises transmitting, by the server, the second graphical user interface to the consumer device.

In another embodiment a method comprises receiving, by a server, a device identifier and location information from a consumer device, the location information being associated with a location of the consumer device and determined from a plurality of location signals received from a plurality of beacons, wherein the device identifier comprises a distinctive combination of at least one of numbers and characters uniquely identifying the consumer device. The method comprises determining, by the server, a current location associated with the consumer device based at least on one of the location information and strength of the location signal received from the plurality of beacons. The method comprises determining, by the server, whether the device identifier from the consumer device and the current location are associated with the consumer device in a database, wherein the database is configured to store a first plurality of records of a first plurality of meal dataset and one or more records of a plurality of consumer devices. The method comprises, in response to the device identifier and the current location being associated with the consumer device in the database, generating by the server, a second plurality of records associated to a second plurality of meal datasets in the database, the second plurality of meal datasets being selected from the first plurality of meal datasets based on availability within a predetermined proximity to the current location of the consumer device. The method comprises receiving, by the server, one or more meal value threshold from the consumer device. The method comprises generating, by the server, a third plurality of records associated to a third plurality of meal datasets, wherein each meal dataset within the third plurality of meal datasets satisfies the meal value threshold. The method comprises generating, by the server, a first graphical user interface configured to display the third plurality of meal datasets. The method comprises, upon transmitting the first graphical user interface to the consumer device, receiving by the server, one or more inputs corresponding to one or more selected meal datasets from the third plurality of meal datasets. The method comprises generating, by the server, a second graphical user interface configured to display instructions to reach one or more physical locations of the one or more selected meal datasets in relation to the current location of the consumer device. The method further comprises transmitting, by the server, the second graphical user interface to the consumer device.

In yet another embodiment, a computer system comprises a server, which is configured to receive a device identifier and location information from a consumer device, the location information being associated with a location of the consumer device and determined from a plurality of location signals received from a plurality of beacons, wherein the device identifier comprises a distinctive combination of at least one of numbers and characters uniquely identifying the consumer device. The server is configured to determine a current location associated with the consumer device based at least on one of the location information and strength of the location signal received from the plurality of beacons. The server is configured to determine whether the device identifier and the current location from the consumer device are associated with the consumer device in a database, wherein the database is configured to store a first plurality of records of a first plurality of meal dataset and one or more records of a plurality of consumer devices. The server is configured to in response to the device identifier and the current location being associated with the consumer device in the database, generate a second plurality of records associated to a second plurality of meal datasets in the database, the second plurality of meal datasets being selected from the first plurality of meal datasets based on availability within a predetermined proximity to the current location of the consumer device. The server is configured to generate a first graphical user interface configured to display the second plurality of meal datasets. The server is configured to upon transmitting the first graphical user interface to the consumer device, receive one or more inputs corresponding to one or more selected meal datasets from the second plurality of meal datasets. The server is configured to generate a second graphical user interface configured to provide instructions to reach one or more physical locations of the one or more selected meal datasets in relation to the current location of the consumer device. The server is further configured to transmit the second graphical user interface to the consumer device.

The plurality of consumer-defined constraints (e.g., meal value thresholds) can be a plurality of rules applied to a plurality of records associated to a plurality of meal choices to identify a plurality of meal choices in compliance with quantitative requirements of one or more of calorific content, ingredients, macronutrient content, and micronutrient content associated with a plurality of meal choices.

The plurality of consumer-defined constraints (e.g., meal value thresholds) can be a plurality of rules applied to a plurality of records associated to a plurality of meal choices to identify a plurality of meal choices in compliance with vegan dietary requirements (e.g., whether the meal dataset indicates a value associated with a vegan value).

The plurality of consumer-defined constraints (e.g., meal value thresholds) can be a plurality of rules applied to a plurality of records associated to a plurality of meal choices to identify a plurality of meal choices in compliance with kosher dietary requirements (e.g., whether the meal dataset indicates a value associated with a kosher value, or other ingredient values corresponding to any quantified attribute associated with the meal).

The plurality of consumer-defined constraints (e.g., meal value thresholds) can be a plurality of rules applied to a plurality of records associated to a plurality of meal choices to identify a plurality of meal choices in compliance with gluten-free dietary requirements (e.g., whether the meal dataset indicates a value associated with a gluten-free value).

Additional features and advantages of an embodiment will be set forth in the description which follows, and in part will be apparent from the description. The objectives and other advantages of the invention will be realized and attained by the structure particularly pointed out in the exemplary embodiments in the written description and claims hereof as well as the appended drawings. It is to be understood that both the foregoing general description and the following detailed description are exemplary and explanatory, and are intended to provide further explanation of the invention as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

DETAILED DESCRIPTION

Figure 1:
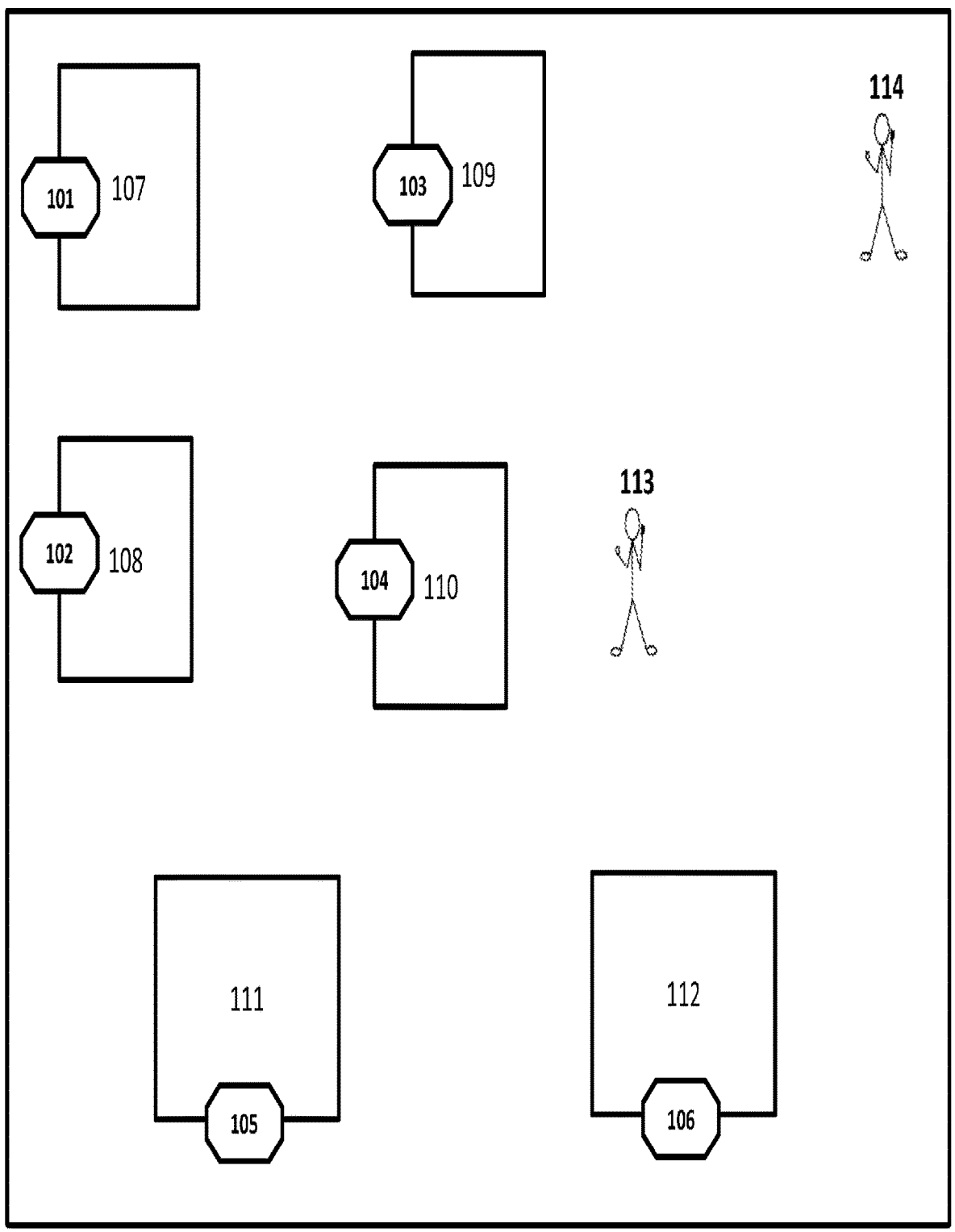
FIG. 1 illustrates an exemplary embodiment, where the beacons are associated to individual food stations.

Reference will now be made in detail to the preferred embodiments, examples of which are illustrated in the accompanying drawings. The embodiments described herein are intended to be exemplary. One skilled in the art recognizes that numerous alternative components and embodiments may be substituted for the particular examples described herein and still fall within the scope of the invention.

The term "beacon" as used herein refers to any device configured to transmit a data packet, which is used by a receiving device to identify the transmitting device and compute the relative distance between the transmitting device and the receiving device. Beacons can be physical devices or virtual beacons. Beacons transmit small packets of data. Currently, beacons repeatedly transmit data packets in set intervals. There are several types of beacons and associated protocols available in the market such as iBeacon system (implemented by Apple®), AltBeacon (provided by Radius Networks), and EddyStone® (from Google®). The iBeacons and AltBeacons broadcast a data packet consisting mainly of following pieces of information-a Universally Unique Identifier (UUID), a major number, a minor number, and a transmission power level known as the "Broadcasting Power." These formats require external databases to give meaning to the beacon data packets. Receiving devices can approximate distance from the beacon by comparing the Broadcasting Power to the strength of the signal as received, known as the Received Signal Strength Indicator (RSSI). As these devices typically transmit that packet over and over again, this type of transmission defines the advertising functionality of beacons. These data packets are recognized only by special apps on the mobile phone of the consumers. Beacons supporting the Eddystone format broadcast three different packets: a unique ID number, a URL address, and telemetrics based on sensors. They don't require an external database; instead they use web links to either link to data directly and could function via a two-way communication method. The Eddystone-URL frame type broadcasts information that can be used by a phone even without a specialized application. Virtual beacons may not require specialized devices and may use existing indoor positioning systems and the consumer devices to deliver location-based information. Beacons can be configured to broadcast sensor data such as temperature and battery level, or even data gathered from other sensors in the room such as infra-red detectors.

The term "device identifier" as used herein refers to a distinctive combination of numbers or characters associated with a particular computing device for the purpose of uniquely identifying that computing device to other devices and systems that are communicatively coupled to it.

The term "de-identification" as used herein refers to the process of removing personal identifiers (i.e. phone numbers, names etc.) to mitigate privacy risks to individuals. Data that has gone through the de-identification process and cannot reasonably be connected or associated to a consumer or a specific computer or mobile device.

The term "location-aware devices" as used herein refers to computing devices that can passively or actively determine their location. Location signal data can be accessed and passed to the computing device in different ways. Location signals that can be detected by location-aware devices can be outdoor signals, indoor signals, or combinations thereof. Outdoor signals can be GPS, Wi-Fi, IP address, cell-tower triangulation, and consumer-reported location. Indoor signals can be A-GPS, indoor positioning system (IPS), and Wi-Fi triangulation. The consumer devices used herein are location-aware devices, such as mobile phones.

Proximity to a location-aware device is determined by applying system-defined or user-defined rules regarding acceptable distance between the food stations and the consumer device. Proximity can be restricted by preset latitude and longitude boundaries based on the consumer device's location data. Proximity can also be determined at least in part based on a preset search radius around the geographic coordinates of the consumer device as the center of the search area. Proximity can also be determined based on a combination of location signals to indicate specific buildings, floors, or facilities where meal choices (e.g., meal datasets) are available.

The term "indoor positioning systems" as used herein refers to any system that attempts to provide an accurate position of a computing device inside of a covered structure. In addition to using location information from a beacon, certain embodiments can use triangulation to assess more accurately the location of a receiving device. For instance, the receiving device may receive signals from more than once source or of more than one type, e.g., Wi-Fi, BLE, and GPS. By relying on more than once source, the reliability and accuracy of the systems and methods disclosed herein are enhanced.

The term "micro-fenced location" as used herein refers to a virtual fenced location defined by indoor positioning systems. The boundaries of a micro-fenced location can be set by a consumer or by an administrator of the nutrition management system.

In an embodiment, beacons are placed in specific areas of the food facility, such as entrances to the cafeteria or food court, hallways, food stations, and meal display areas. FIG. 1 is an illustration of the various components of a nutrition management system in accordance with an exemplary embodiment. Here, each one of the individual food stations 107, 108, 109, 110, 111, and 112 has a beacon 101, 102, 103, 104, 105, and 106 associated with it. Each beacon can be configured such that the location signal range encompasses approximately the boundaries of the food station. For example, beacon 101 associated with food station 107 can have a 2 ft location signal range, beacon 103 associated with food station 109 can have a 4 ft location signal range, and beacon 106 associated with food station 112 can have a 7 ft location signal range. Beacons 102 and 111 associated with food stations 108 and 111 can be short range transmission beacons, in order to avoid across-the-station cross-transmission issues. When a consumer device 113 is within the location signal range of any one of the beacons, such as beacon 104 associated with food station 110, then a receiver in the consumer device 113 detects the location signals from beacon 104 and communicates them to an application program. For example, beacon 104 broadcasts the following data packet UUID 119 886 533 200 13 Major: 41 Minor: 1. The consumer device 113 receives this data packet and determines that it is from beacon 104 situated in food station 110 on a certain floor in a specific building of company X, and transmits this information along with a device identifier or a user identifier associated with the consumer device 113 to the nutrition management server via the application program. The nutrition management server then queries (e.g., instructs a database to receive) an associated nutrition management database to retrieve information associated with meals available at food station 111, such as ingredients, nutritional content, presence of allergens, and mode of preparation. The nutrition management sever may generate a meal dataset comprising all the information pertinent to the mean. The meal dataset is then presented back to the user of the consumer device 113. The user interface on the consumer device 113 can be configured to present options to the user, such as options pay for the meal at that instant via online payment systems, provide comments, or upload the information regarding the meal choice to other application program such as the calorie intake to a fitness tracker app.

FIG. 1 also illustrates another exemplary embodiment, where a user accesses the nutrition management server using his device 114 and submits a request for a particular meal choice. The nutrition management server then presents the results of the query on the device 114 through interfaces such as those presented in FIGS. 3, 4, and 5. The user can also request view of meal choices to meet special dietary requirements, such as vegan, kosher, or gluten-free. The meal choices and associated information can be viewed in any format or combination as required by the consumer. A person skilled in the relevant art will appreciate that the nutritional management server may generate a meal dataset, which comprises all the pertinent information regarding the meal (e.g., nutritional information, pictures, and the like). The words "meal," "meal choice," and "meal dataset" mean the same and have been interchangeably used throughout the present disclosure.

Figure 2:
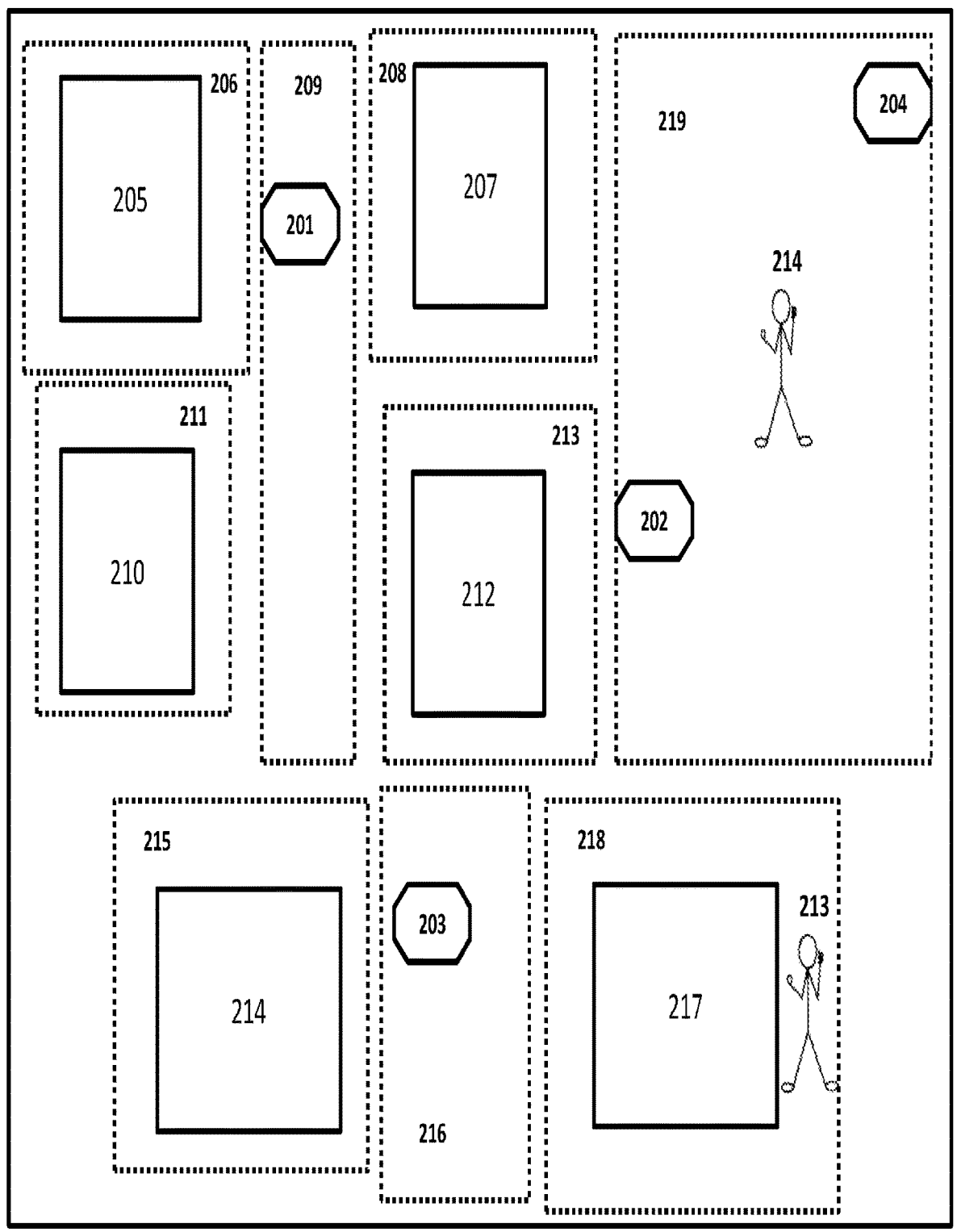
FIG. 2 illustrates an exemplary embodiment, where the beacons are utilized to generate micro-fenced food stations.

FIG. 2 is an illustration of the various components of a nutrition management system in accordance with an exemplary embodiment. Here, the beacons 201, 202, 203, and 204 are placed in specific areas of a food facility, such as entrances to the cafeteria or food court, hallways, food stations, and meal display areas, but the beacons are not associated with each of the food stations 205, 207, 210, 212, 214, and 217. Instead, information associated to a diagrammatic representation of the physical floor plan is provided to the nutrition management database. A dataset containing strength and composition of the location signals from various beacons throughout the entire floor is created, by the nutrition management server, and overlaid on the diagrammatic representation of the physical floor plan. Thus, granular portions of the physical floor plan are associated to strength and composition of the location signals from various beacons to create several micro-fenced locations, such as micro-fenced location 206 around food station 205, micro-fenced location 208 around food station 207, micro-fenced location 211 around food station 210, micro-fenced location 213 around food station 212, micro-fenced location 215 around food station 214, micro-fenced location 218 around food station 217, micro-fenced location 209 as the moving space between food stations 205, 207, 210, and 212, or the large entrance 219 to the food facility. In this embodiment, individual beacons need not be moved regularly due to floor plan changes or in companies that have flexible, adaptable food service areas. Therefore, when the cafeteria wants to combine two or more individual food stations to form a larger one, then a simple upload of the diagrammatic representation of the new floor plan, by the nutrition management server, will be sufficient to recalibrate the nutrition management program to adapt to the new floor plan and create new micro-fenced locations. Using beacons as shown in FIG. 2 results in a dynamic meal availability map with virtual fenced locations. At a given point, a mobile application on a user device may detect different location signals with certain signal strengths. This set of location signals and their associated signal strengths represents a datapoint that is unique to that physical position. In other embodiments, the users can request the desired resources, navigate the hallways to the physical location of the food stations, and request friends to meet them at particular stations with the use of their devices.

For example, as illustrated in FIG. 2, a limited dataset containing strength and composition of the location signals from the beacons 201, 202, 203, and 204, and corresponding to the food station 217 defines the micro-fenced location 218. When a consumer device 213 is outside the food station 217, the receiver in the consumer device 213 detects the location signals from the beacons 201, 202, 203, and 204. The device 213 communicates them along with a device identifier or a user identifier associated with the consumer device 213 to the nutrition management server via an application program. The unique combination of strength and composition of the location signals from device 213 is used to determine that the device is within the micro-fenced location 218. The nutrition management server then queries (e.g., generates and transmits an instruction to receive) an associated nutrition management database to retrieve information associated with meals available at food station 217, such as ingredients, nutritional content, presence of allergens, and mode of preparation. This information is then presented back to the user of the consumer device 213 to make a particular meal choice, based on consumer-defined rankings, such as list low carb food first, or high-protein foods first, or present the foods in increasing value of points of the Weight Watchers® plan.

FIG. 2 also illustrates another exemplary embodiment, where a user accesses the nutrition management server using his device 214 and submits a request for a particular meal choice. The nutrition management server then presents the results of the query on the device 114 through interfaces such as those presented in FIGS. 3, 4, and 5. The user can also request view of meal choices (e.g., a plurality of meal datasets) to meet special dietary requirements, such as vegan, kosher, or gluten-free. The meal choices and associated information can be viewed in any format or combination as required by the consumer. In other instances, transmission of locations signals corresponding to micro-fenced locations 218 and 219 to the nutrition management server can result in the user interfaces on devices 213 and 214 being configured to present a variety of other options, such as an option to access a map showing the location of the various food stations and the route to get to the desired food station.

In an embodiment, on a periodic basis, such as daily or thrice a day or right before meal-time, the app checks the nutrition database and downloads the available menus and meal options for that day in the cafeteria or food court that is set-up with beacons or various micro-fenced locations. So at a predetermined or consumer-defined time before a meal, the app can automatically push a notification regarding the available meal choices onto the user interface of the consumer device. The consumer can review his choices, their nutritional content, mode of preparation, and other information, and choose a particular meal (e.g., meal dataset). Then, when this consumer goes to the food court or a cafeteria with beacons as shown in FIG. 1 or micro-fenced locations as shown in FIG. 2, the app on his mobile device receives the signal from the beacons and transmits the location of the consumer device to a nutrition management server. The application program on his device presents a heat map or other navigational tools, such as those presented in FIGS. 3, 4, and 5, directing the consumer to the exact location where his meal choice is available.

In an embodiment, when a person enters a food court or a cafeteria with beacons as shown in FIG. 1 or micro-fenced locations as shown in FIG. 2, the app on his mobile device receives the signal from the beacons and transmits the location of the consumer device to a nutrition management server. Responsive to this location information, the nutrition management server sends a notification to the user interface on the consumer device, asking the consumer if he wants assistance in making a meal choice. And when the consumer responds affirmatively, the user interface is configured to present various options to make meal choices. For example, the user interface can be configured to present the consumer with the available menus (e.g., meal dataset available), accept a meal choice input from the consumer, and display the nutritional content of his meal choice. Or, the user interface can be configured such that the consumer is presented with nutritional profiles, such as high-protein, or low-fat, or to display Weight Watchers®-friendly profiles, and responsive to the consumer's selection of a particular profile, suitable meal choices can be presented.

In another embodiment, the consumer can set up his profile with his dietary preferences on the app (e.g., threshold values associated with meal datasets such as a caloric threshold, vegan threshold, and the like), such that the app automatically makes suggestions based upon those dietary preferences when the consumer enters a pre-designated place such as the cafeteria or food court. The consumer can customize the mobile application based on height, gender, age, allergy triggers, medication-based restrictions, dietary preferences, current and desired weight and BMI, exercise regimen, and other parameters. For example, if the consumer has set his profile to adhere to a Weight Watchers® plan, then the app connects to the nutrition database, and downloads only the meal choices available at the cafeteria that are suited to the Weight Watchers® plan. In another embodiment, there is a notification from the nutrition management server that consumer X has five meal options suitable to his Weight Watchers® plan. The application can further include a feature whereby the five suitable meal options are further ranked based on the PointsPlus® value, and suggestions are made based on the consumer's PointsPlus® daily target. These five suitable meal options can also be presented to the user in the form of a heat map or navigational tool, such as those presented in FIGS. 3, 4, and 5, directing the consumer to the exact location where the meal choice is available.

In another embodiment, when a consumer enters a food court or a cafeteria with beacons as shown in FIG. 1 or micro-fenced locations as shown in FIG. 2, the app on his mobile device receives the signal from the beacons and transmits the location of the consumer device to a nutrition management server. Based on this location, the app on the consumer device receives a notification presenting the locations, where meals conforming to his dietary restrictions are available, such as kosher meals or gluten-free meals. Once the consumer chooses a particular meal, then a navigational tool is presented to the consumer. This navigational tool can be a heat map (e.g., a color coded map) or navigational tool, such as those presented in FIGS. 3, 4, and 5, showing the top three locations, where meal choices best suited to his preferences are currently available for his consumption.

Figure 3:
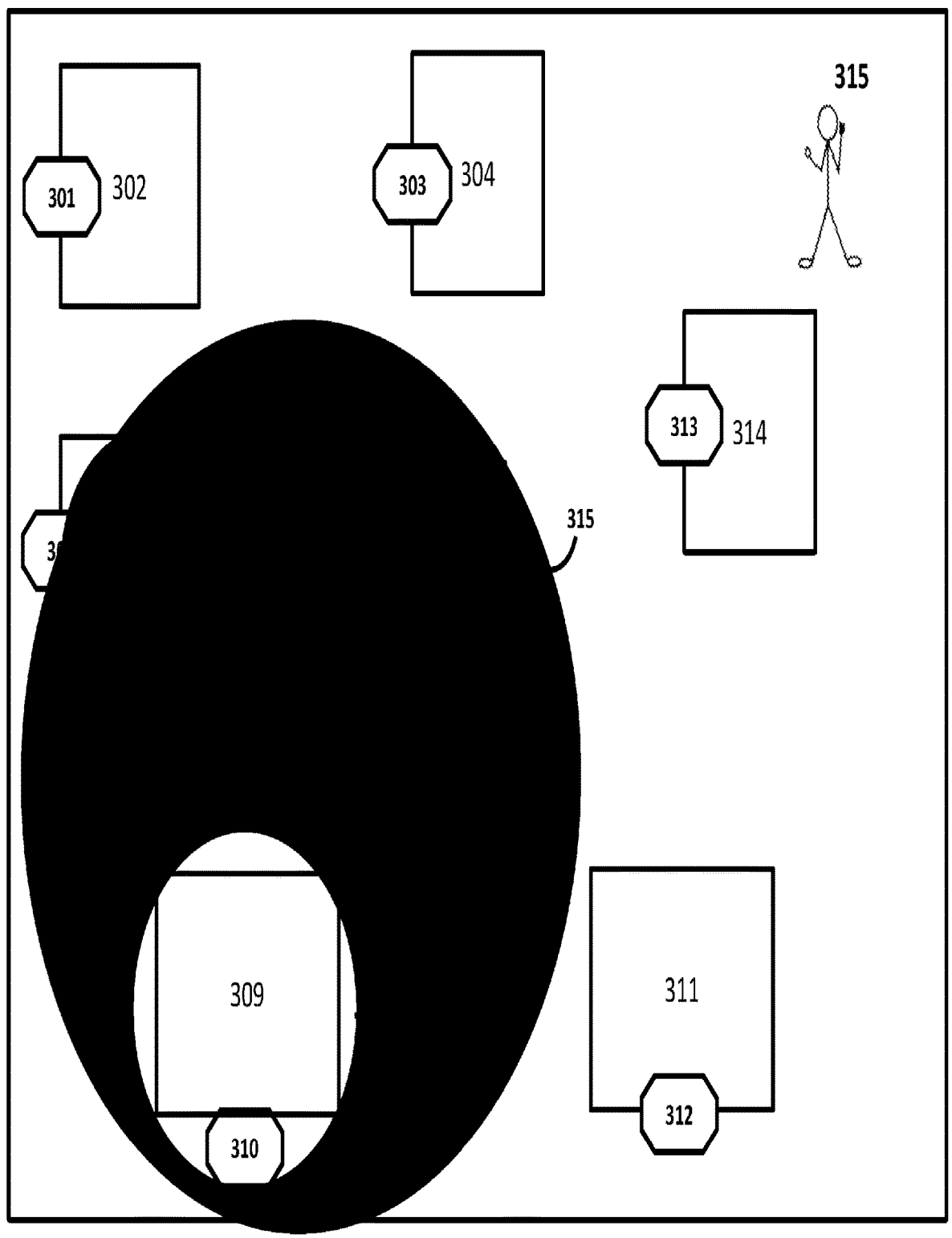
FIG. 3 is an illustration of a user interface displayed on a consumer device in accordance with an exemplary embodiment.

FIG. 3 is an illustration of a user interface displayed on a consumer device in accordance with an exemplary embodiment. Although here, each one of the individual food stations 302, 304, 306, 308, 309, 311, and 314 has a beacon 301, 303, 305, 307, 310, 312, and 313 associated with it, this interface can work with micro-fenced embodiments shown in FIG. 2. Each beacon can be configured, by the nutrition management server, such that the location signal range encompasses approximately the boundaries of the food station. A consumer sets up his profile with his dietary preferences on the app on his device 315, such that the nutrition management server automatically makes suggestions based upon those dietary preferences when the consumer enters a pre-designated place such as the cafeteria or food court. For example, if the consumer has set his profile to adhere to a Weight Watchers® plan, then the app connects to the nutrition management server that then queries (e.g., generates instructions to query) the nutrition management database for appropriate meal choices. Only the meal choices (e.g., meal datasets) available at the cafeteria that are suited to the Weight Watchers® plan are retrieved and analyzed by the nutrition management server to present five meal options suitable to the consumer's Weight Watchers® plan. The application, managed and operated by the nutrition management server, then creates a heat map, which can have shades of grey as shown in FIG. 3, where food stations with more meal choices with smaller PointsPlus® values are represented by dark gray circles (pixels) and food stations with fewer meal choices with larger PointsPlus® values are represented by lighter grey circles. In FIG. 3, the zone of light grey color 315 indicates a zone of food stations that have foods suitable to the consumer's Weight Watchers® plan preferences or recommendations for that point in time. The zone of medium grey color 316 indicates a food station, which has one of the five recommended meal options, and the zone of dark grey color 317 indicates a food station, which has four of the five recommended meal options. Thus the consumer is directed, by the nutrition management server, to the exact location where the most suitable meal choices are available. This heatmap can be in shades of colors going from red for non-friendly options to solid green for the most friendly options, according to any dietary plan.

Meal choices available in the cafeteria can be color coded, by the nutrition management server, based on their energy content or calorific value, or macronutrient types, or any other predetermined or consumer-defined parameter, for example meal choices with the lowest or desired values in green and the largest or less-friendly values in red level, passing through a yellow level in the middle. These color coded heatmaps displayed on the consumer devices makes the consumption of desired meals so much easier and helps the consumer adhere better to a dietary plan. The nutrition management server is configured to retrieve (e.g., generate an instruction to query and receive) tremendous amount of quantitative and qualitative data and execute analyses to generate visual representations that enable consumers to easily choose a meal without agonizing over numbers, labeling issues, and other calculations. A person skilled in the relevant art will appreciate that the nutritional management server may also generate a meal dataset, which comprises all the pertinent information regarding the meal (e.g., nutritional information, pictures, and the like). The nutritional management server may generate a meal value within the meal dataset, which corresponds to different information regarding the meal. Non-limiting examples of a meal value may include, a kosher value indicating whether the meal is kosher, a caloric value indicating the calories associated the meal, and a gluten-free value indicating whether the meal is gluten free. The words "meal" and "meal dataset" have been interchangeably used throughout the present disclosure.

Figure 4:
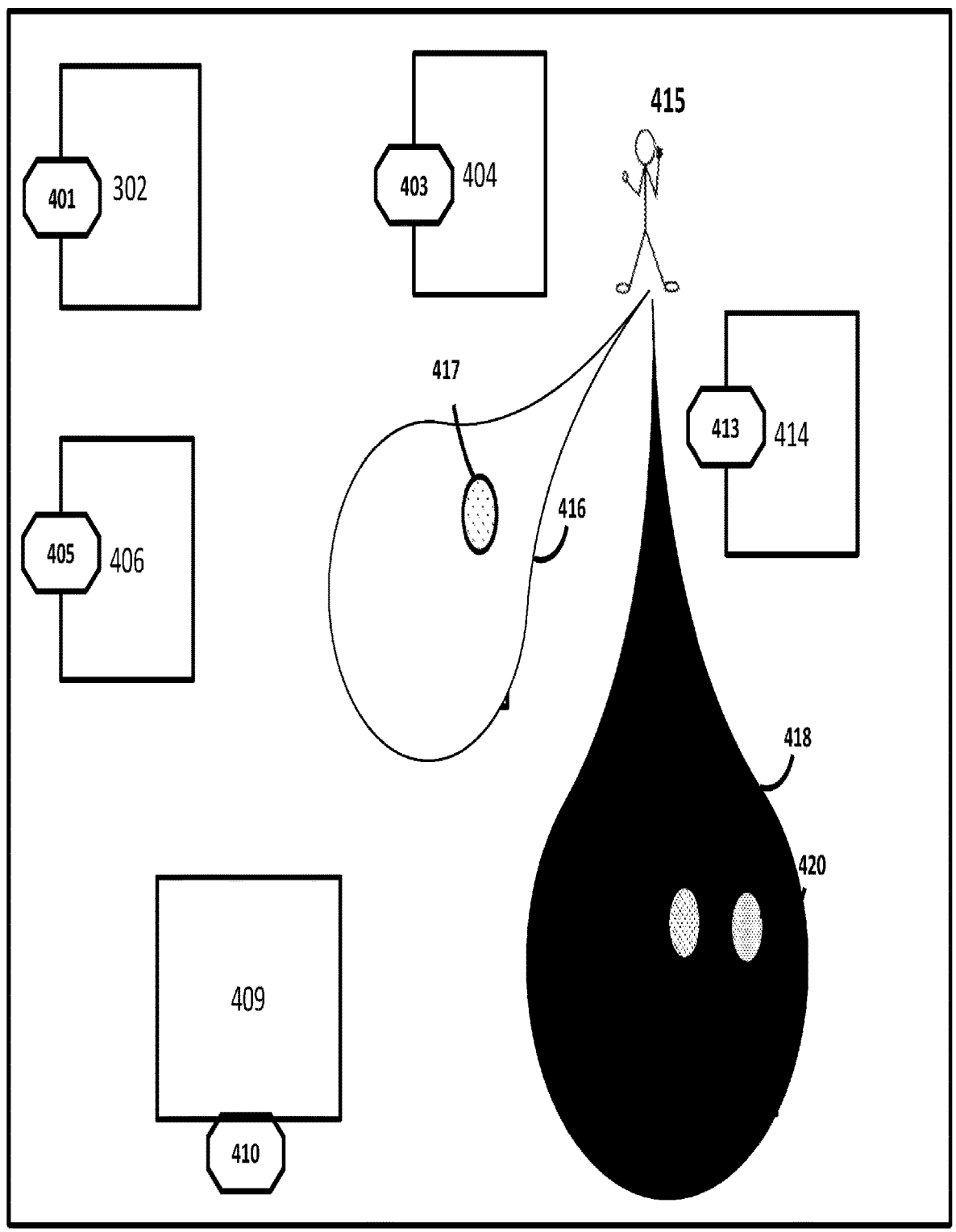
FIG. 4 is an illustration of a user interface displayed on a consumer device in accordance with an exemplary embodiment.
Figure 5:
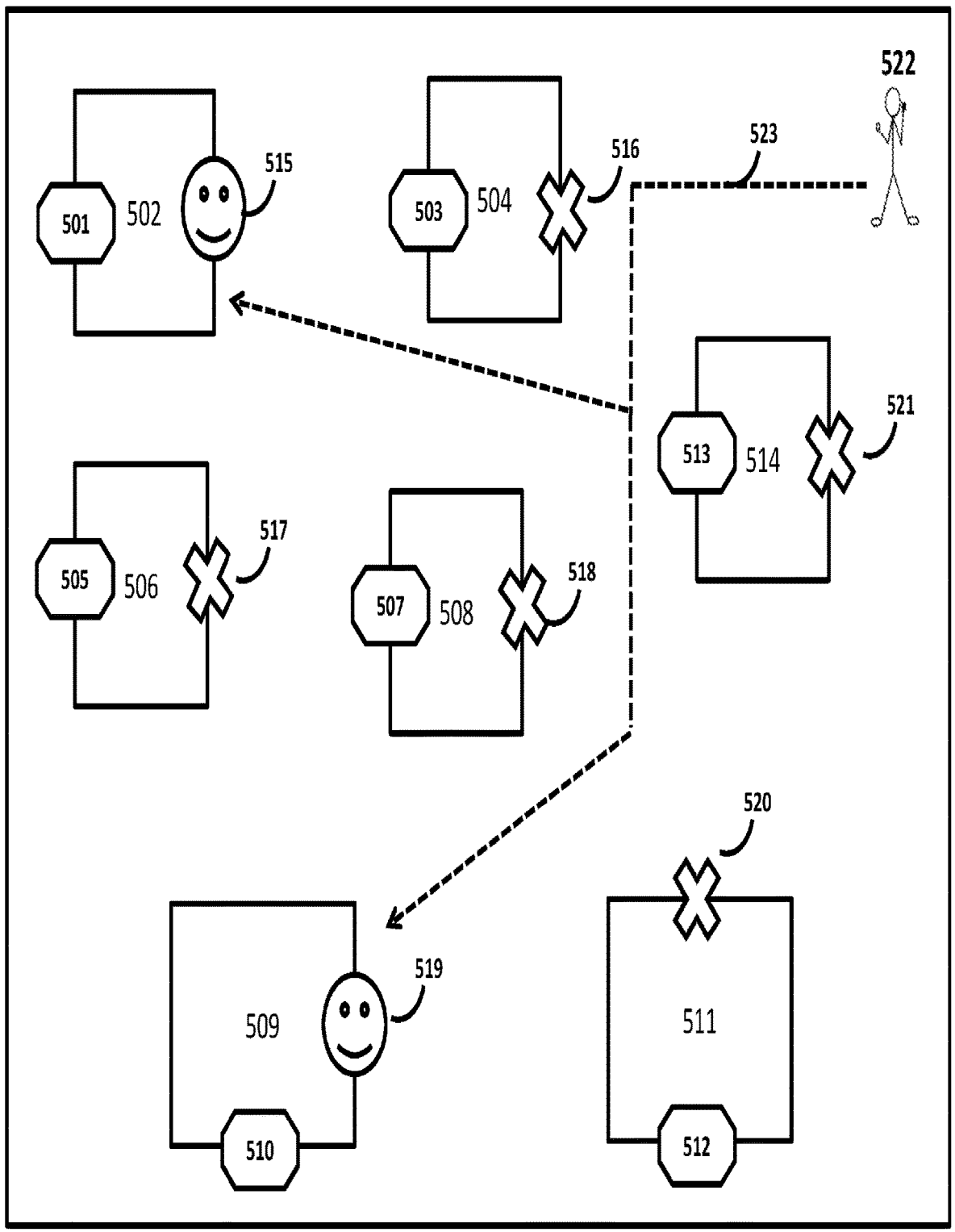
FIG. 5 is an illustration of a user interface displayed on a consumer device in accordance with an exemplary embodiment.

FIG. 4 is an illustration of a user interface displayed, by the nutrition management server, on a consumer device in accordance with an exemplary embodiment. Although here, each one of the individual food stations 402, 404, 406, 408, 409, 411, and 414 has a beacon 401, 403, 405, 407, 410, 412, and 413 associated with it, this interface can work with micro-fenced embodiments shown in FIG. 2. Each beacon can be configured, by the nutrition management server, such that the location signal range encompasses approximately the boundaries of the food station. A consumer sets up his profile with his dietary preferences on the app on his device 415, such that the app, operated and managed the nutrition management server, automatically makes/displays suggestions based upon those dietary preferences when the consumer enters a pre-designated place such as the cafeteria or food court. For example, if the consumer has set his profile to adhere to an Atkins® plan, then the app connects to the nutrition management server that then queries the nutrition management database for appropriate meal choices. Only the meal choices available at the cafeteria that are suited to the Atkins® plan are retrieved and analyzed by the nutrition management server to present meal options suitable to the consumer's Atkins® plan. The application then creates a trail map, which can have shades of grey as shown in FIG. 4, where food stations with more meal choices that are Atkins® plan friendly are represented by dark gray trailing balloons and food stations with fewer meal choices that are less Atkins® plan friendly are represented by lighter grey trailing balloons. In FIG. 3, the zone of light grey color 416 indicates a food station that has a few food choices suitable to the consumer's Atkins® plan preferences or recommendations. Depending on the amount of information in the nutrition management database, the user interface can be configured, by the nutrition management server, to display even more granular information to the consumer, such as the Atkins® plan friendly meal choices are situated in the highlighted zone 417 at food station 408. The zone of dark grey color 418 indicates a food station 411, which has two recommended meal options shown as highlighted zones 419 and 420 and each of the zones can be coded to be more or less friendly to the plan. Thus, the consumer device is directed, by the nutrition management server, to the exact location where the most suitable meal choices are available.

FIG. 5 is an illustration of a user interface displayed on a consumer device, by the nutrition management server, in accordance with an exemplary embodiment. Although here, each one of the individual food stations 502, 504, 506, 508, 509, 511, and 514 has a beacon 501, 503, 505, 507, 510, 512, and 513 associated with it, this interface can work with micro-fenced embodiments shown in FIG. 2. Each beacon can be configured, by the nutrition management server, such that the location signal range encompasses approximately the boundaries of the food station. In some embodiments, a consumer sets up his profile with his dietary preferences on the app on his device 522, such that the app, operated and managed by the nutrition management, automatically makes suggestions based upon those dietary preferences when the consumer enters a pre-designated place such as the cafeteria or food court. For example, if the consumer has set his profile to adhere to a TLC Diet or DASH plan, then the app connects to the nutrition management server that queries (e.g., generates and transmits an instruction to query the data) the nutrition management database for appropriate meal choices. Only the meal choices available at the cafeteria that are suited to these plans are retrieved and analyzed by the nutrition management server to present meal options suitable to the consumer's Atkins® plan. The application, managed and operated under instructions from the nutrition management server, configures the user interface to display a trail map including the routes 523 to food stations 502 and 509 with more suitable meal choices that are indicated with icons, such as happy faces 515 and 519. Food stations 504, 506, 508, 511, and 514 with fewer or no suitable meal choices are represented by icons, such as big crosses 516, 517, 518, 520 and 521. Depending on the amount of information in the nutrition management database, the user interface can be configured, by the nutrition management server, to display even more granular information to the consumer, such as where the particular meal choices best suited to the TLC Diet or DASH plan are situated in the highlighted food stations 502 and 509. Thus the consumer is directed to the exact location where the most suitable meal choices are available.

In another example, the user interface can be configured, by the nutrition management server, to send a haptic alert such as a tap or a vibrating buzz to the consumer device when the consumer is near food stations that offer diet plan-friendly meal options. The consumer does not have to retrieve his mobile phone and review the recommended food stations. If the consumer is using a wearable device, such as a watch or a band or a locket, then a haptic alert can be sent, by the nutrition management server, to that device, along with a visual message to the phone. This haptic alert can be customized to be distinct from the regular alert for text and mails.

The application program can also be configured, by the nutrition management server, to include a dietary tracking tool that monitors nutritional content and quantity of food consumption. And based on historical data associated with the consumer, the application program can also be configured to make suggestions addressing nutritional deficiencies or better-suited options. For example, the nutrition management server can analyze the consumer's meal choices for the a predetermined period of time, such as for the past seven days, and determine that there is insufficient fiber consumption based on the meal choices. Then, the menus for the upcoming week can be analyzed to identify meal choices with high fiber content. During meal times when these choices are available, the user interface can display these meal suggestions. Or, if the analysis of the menus for the upcoming week yields no appropriate meal choices with high fiber content, then a notification can be sent, by the nutrition management server, to the consumer to seek such nutritional content in other meal choices. In another aspect, this information regarding nutritional issues can also be communicated, by the nutrition management server, back to the administrator of food services or the entity managing the cafeteria. Data from this mobile application regarding dietary consumption can be shared, by the nutrition management server, with other application programs, such as the fitness monitoring apps or lifestyle apps. A person skilled in the relevant art will appreciate that the nutrition management server may compare the values within the meal dataset with a dietary threshold in order to analyze the consumer's meal choices. For example, the nutrition management server may compare a value associated with the caloric content of a meal dataset of a consumed meal to a calorie-intake threshold for that consumer.

In another aspect, the consumer can also customize his profile to indicate any ingredients or compounds that trigger allergic reactions. When the nutrition management server detects a meal choice dataset that contains one of those allergens (e.g., the meal dataset value indicates that the allergen is present within the meal), an alert in the form of a text alert or a haptic alert such as a violent tap or a vibrating buzz is sent to the consumer device.

In another embodiment, the computer-implemented method includes communicating, by the nutrition management server, meal choices (e.g., meal datasets selected by the consumer) with a consumer device in compliance with consumer-defined constraints. The method includes receiving, by one or more server computers (e.g., the nutrition management server), a device identifier and location information from a consumer device. As shown in FIGS. 1 and 2, the location information is associated to current location of the consumer device and determined from a plurality of location signals received from a plurality of beacons. In a next step, the one or more server computers verify the device identifier and the location information from the consumer device as being associated with the consumer device in a database configured to store a first plurality of records of the first plurality of meal choices and one or more records of a plurality of consumer devices. The one or more server computers retrieve a second plurality of records associated to a second plurality of meal choices in the database selected from the first plurality of meal choices based on availability within a predetermined proximity to the current location of the consumer device. In some embodiments, the predetermined proximity is received from a client mobile device. The one or more server computers then apply a plurality of consumer-defined constraints on the second plurality of records associated to a second plurality of meal choices to determine a third plurality of records associated to a third plurality of meal choices, and generate on the consumer device a first graphical user interface configured to display the third plurality of meal choices. The one or more server computers then receive one or more inputs corresponding to one or more selected meal choices from the third plurality of meal choices via the first graphical user interface at the consumer device. The one or more server computers generate, in response to receiving one or more selected meal choices, a second graphical user interface on the consumer device configured to provide instructions to reach one or more physical locations of the one or more selected meal choices.

The plurality of consumer-defined constraints can be a plurality of rules applied to a plurality of records associated to a plurality of meal choices to identify a plurality of meal choices in compliance with quantitative requirements of one or more of calorific content, ingredients, macronutrient content, and micronutrient content associated with a plurality of meal choices. For example, the one or more servers, may receive from the consumer device a value threshold associated with the constraint and determine whether the meal dataset presented satisfies the value threshold. In that example, if the meal dataset satisfies the constraint, then the nutrition management server may not display the meal dataset or the physical location associated with that meal to the consumer. The plurality of consumer-defined constraints can be a plurality of rules applied to a plurality of records associated to a plurality of meal choices to identify a plurality of meal choices in compliance with vegan dietary requirements. The plurality of consumer-defined constraints can be a plurality of rules applied to a plurality of records associated to a plurality of meal choices to identify a plurality of meal choices in compliance with kosher dietary requirements. The plurality of consumer-defined constraints can be a plurality of rules applied to a plurality of records associated to a plurality of meal choices to identify a plurality of meal choices in compliance with gluten-free dietary requirements.

In an embodiment, each meal choice available at the various food stations are assigned a particular set of values (e.g., values within the meal dataset), the values corresponding to certain characteristics of the meal choices, including but not limited to calories, diet restrictions, ingredients, macronutrient contents, micronutrient contents, and other values associated with one or more of Weight Watchers®, Atkins®, South Beach Diet®, TLC Diet or DASH plans. These values are all stored in the nutrition management database, and these values are analyzed based on depending on any consumer-defined constraint or predetermined rules. For example, each characteristic of a consumer-defined constraint is given a value based on the preferred meal choices, including but not limited to calories, diet restrictions, ingredients, macronutrient contents, micronutrient contents, and other values associated with one or more of Weight Watchers®, Atkins®, South Beach Diet®, TLC Diet or DASH plans. When a consumer makes a meal choice, the nutrition management server compares the value attributes of the consumer's preferred meal choices to the value attributes of the meal choices available that day in the cafeteria to generate one or meal choices whose value attributes match the value attributes of the consumer's preferred meal choices. The consumer can designate a priority ranking for each of the several value attributes of the meal choices. For example, the consumer can input the following: when foods have same sugar content, choose foods containing naturally occurring sugars rather than food containing processed sugars or when foods contain the same protein content, choose foods containing non-animal protein rather than foods containing animal protein; or when foods have the same calories, choose foods containing more protein content rather than foods containing more carbohydrate content.

Figure 6:
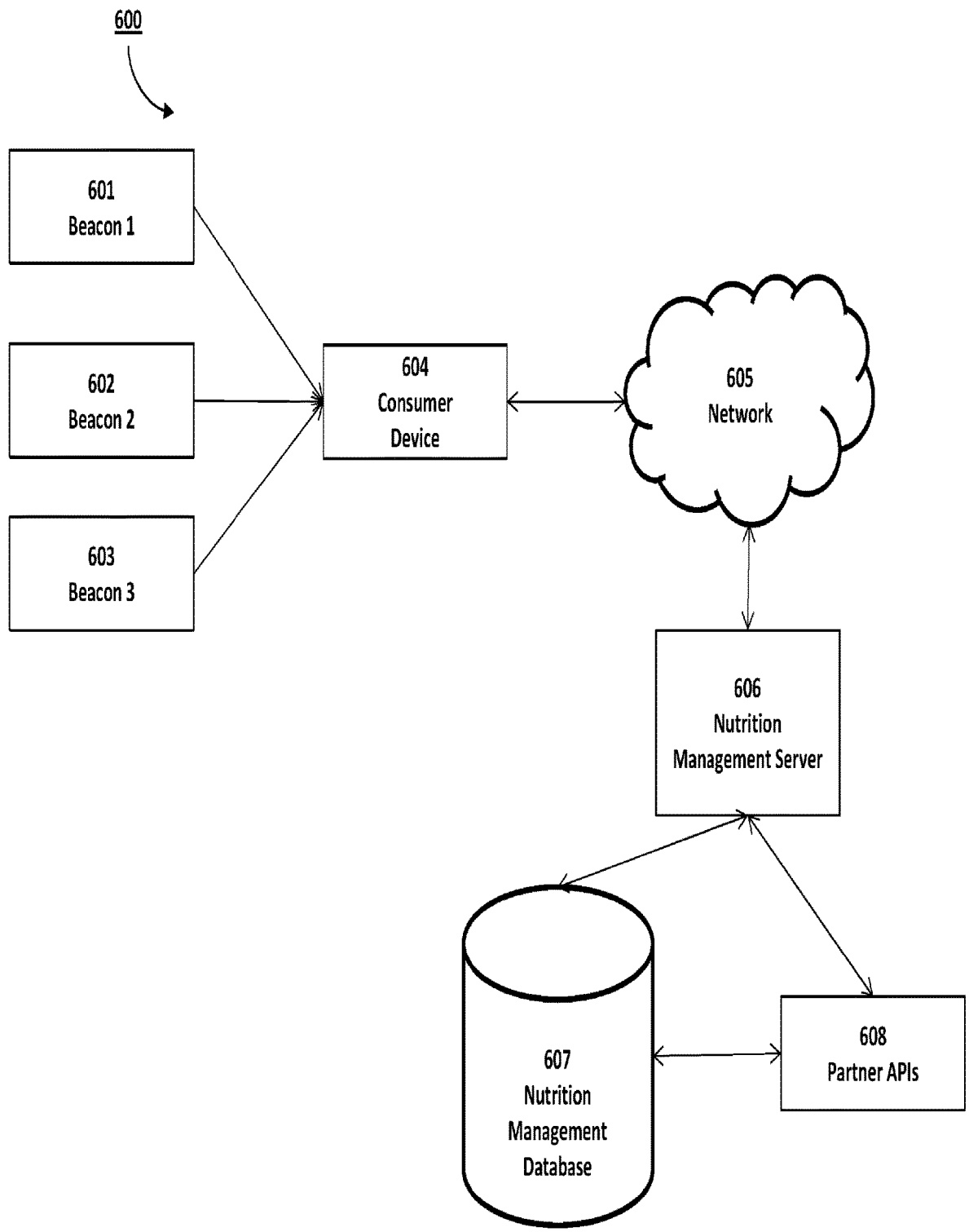
FIG. 6 is a block diagram illustrating a system containing a nutrition management server, according to an embodiment.

Certain embodiments include a system for communicating information between a nutrition management database, a consumer device, one or more beacons, and a nutrition management server. FIG. 6 is a block diagram illustrating a system 600 containing a nutrition management server, according to an embodiment. A plurality of beacons, for example 601, 602, and 603 transmit a plurality of location signals that are received by a consumer device 604. The device 604 then transmits a device identifier and the plurality of location signals from the plurality of beacons 601, 602, and 603 via a network 605 to one or more servers constituting the nutrition management server 606. The system includes a nutrition management database 607 hosted by or communicatively coupled to the nutrition management server 606. The nutrition management database 607 is configured to store one or more records of a plurality of consumer identifiers, unique device identifiers, individual dietary and allergy profiles, individual meal preferences, calendars corresponding to available meal choices at the various food facilities, meal choices based on dietary plans such as Weight Watchers®, Atkins®, South Beach Diet®, TLC Diet or DASH plan, other nutritional information, including but not limited to calorific content, ingredients, macronutrient content, and micronutrient content, and all combinations thereof.

The consumer device 604 can be any mobile location-aware computing devices, e.g., wearables, smartphone or tablets, that can receive a wireless signal from one or more transmitters of location signals. When the consumer device 604 receives the location signals, it can process it using one or more mobile applications in communication with one or more servers constituting the nutrition management server 606. Mobile applications of the nutrition management system, managed and operated by the nutrition management server, can be implemented as software that can be downloaded and installed on the consumer device 604. Examples of mobile application are GUI applications that may be available at, downloaded, and installed from a public software app stores or digital application distribution platforms, such as Apple iTunes®, Google Play® Store and Amazon.com®, among others. In these embodiments, mobile application includes the following exemplary functions: allowing the consumer to create and manage a consumer account, nutrition and allergy profiles, and other preferences within the nutrition management system 600; allowing the consumer to see the available meal choices associated with particular physical locations or micro-fenced locations, allowing the consumer to receive communications such as calendar notifications, e-mails or text messages from the nutrition management system 600; and allowing the consumer to see updates or modifications or other status reports or options for further action and instructions from the nutrition management system 600.

The mobile application can have a landing graphical consumer interface or an introductory interface where the consumer enters his credentials to the nutrition management system 600. Upon entering proper credentials, the consumer is presented with graphical consumer interfaces that present, collect, and communicate information to and from the nutrition management system 600. One or more consumer-side and server-side technologies or combinations thereof can be implemented to ensure that the graphical consumer interfaces are dynamically generated based on the updates to the records in the nutrition management database 607.

Content for personalized web-based or an app-based interfaces can be dynamically generated on consumer devices, based on updates to the nutrition management database 607 and plurality of inputs from the location-aware devices. The information presented to the consumer devices can be subject to de-identification, depending on the security levels or the "need-to-know" level associated with various consumers of the nutrition management system 600. Data communicated between the various devices, servers, and other components of the system is encrypted, stored, decrypted, and distributed using one or more firewalls, antivirus and antiphishing software, file encryption protocols, and other encryption software.

In some embodiments, the UUIDs or unique identifiers of the beacons 601, 602, and 603 must be programmed and associated with particular locations where they are installed. The beacons 601, 602, and 603 continuously broadcast information, for example in the form of data strings, at a predetermined interval, like a heartbeat of data broadcasts, which are then captured by one or more applications on the consumer devices. The data fields in these broadcasted data strings could include an identifier of an individual beacon, location of the beacon in the office space, time of day, and any information designed for consumption by the consumer devices.

A nutrition management server 606 may be any computing device, including one or more servers, comprising non-transitory machine-readable storage media, processors, and software modules capable of performing various tasks and processes described herein. In an embodiment, an application can be downloaded to a consumer device that is able to communicate with the server. The application can be created and maintained by same party who maintains the nutrition management server 606. In certain embodiments, component features of the server may reside on separate physical devices.

The nutrition management database 607 is a body of information associated with the meal choices available in a workspace or food facility or company, and organized as records. This database can comprise information regarding individual consumers such as available consumer devices, profiles, preferences, meal choice history from a particular consumer device, and payment information, and shared resources such as information regarding food stations, other consumer reviews, online event calendar, and available discounts. Information in these databases can be stored or retrieved dynamically using appropriate storage management software. For example, a database in some embodiments can be a database containing information regarding the beacons 601, 602, and 603, their locations, online calendars associated to them, or any information for the consumer. The database can be part of the server, however, in some embodiments the database may reside on a different computing device than the server (i.e., a distributed computing environment).

The system includes a network 605, which is any common communication architecture that facilitates communication between computing devices. For example, the computing devices communicating over the network 605 would be the one or more receiving devices, one or more beacons 601, 602, and 603, a network server, and one or more databases. One having ordinary skill in the art would appreciate that the network may be the Internet, a private intranet, or some hybrid of the two. The network 605 may be comprised of any combination of devices and protocols capable of facilitating communication between computing devices. Non-limiting examples of devices comprising the network 605 may include routers, switches, hubs, firewalls, proxy servers, telecommunications trunks, and the like. Non-limiting examples of protocols employed by the network may include TCP/IP, Wi-Fi, Bluetooth®, 3G, Wi-Max, and the like. Wireless communication between one or more consumer devices and one or more transmitters may be performed with a relatively short-range wireless communication protocol such as Wi-Fi, Bluetooth, high frequency systems, or other relatively localized wireless communication protocols.

Beacons 601, 602, and 603 may be any computing or other electronic device comprising a processor and a wireless interface capable of transmitting signals to a receiving device. The signals may contain binary data, and the binary data may represent various types of data and/or information for the consumer device 604 to consume and implement. The components of the consumer device 604 receiving the signals, may translate the signals into useful binary data triggering various tasks and process according to the application executed by the consumer device 604. The beacons 601, 602, and 603 may implement any suitable components for wirelessly communicating with the consumer device 604, or other receivers. The technological components may include wireless networking hardware and the related protocols, such as a Bluetooth low energy (BLE) interface chip and the Bluetooth wireless communication protocols.

Although FIG. 6 shows only a limited number of beacons 601, 602, and 603, it should be appreciated that more transmitters may be communicatively coupled to one another, over a wired and/or wireless network of transmitters. That is, locations, such as brick-and-mortar office buildings, schools, campuses of multiple buildings, governmental or administrative buildings, and the like, may implement localized networks of beacons to transmit and/or collect data, across a broader area. Furthermore, although the exemplary system described in FIG. 6 describes a stationary beacons 601, 602, and 603, it should also be appreciated that beacons 601, 602, and 603 may be any suitable stationary or mobile devices that are capable of performing the various tasks and processes described herein. Thus, a collection of beacons 601, 602, and 603 can comprise an combination of mobile and stationary devices. It should also be appreciated that, although FIG. 6 describes beacons 601, 602, and 603 performing one-way signal transmissions, beacons 601, 602, and 603 may be capable of two-way communications (i.e., collecting data from signals transmitted by receiving devices), and may be capable of a number of functions or execute a variety of software modules. Non-limiting examples of beacons 601, 602, and 603 may include an iBeacon, AltBeacon, and EddyStone, a wireless router, a cellular phone, a tablet, a wearable, a workstation, or any other suitable computing or other electronic device. The data strings from the beacon can comprise both constant identifiers that do not change with every broadcast and dynamic identifiers that change with every broadcast.

In some instances, certain plurality of records can be provided by a partner application programmable interfaces (API) 608 associated to the nutrition management server 306 configured to process records associated with meal choices available at one or more facilities or workspaces. The APIs 308 can be any Representational State Transfer Application Programming Interface (REST API) that controls and manages one or more APIs. In these embodiments, API provides web services to one or more mobile applications installed on the computing devices. Examples of web services include showing data on a website, uploading large amounts of data that will later be consumed by a mobile app, downloading data to run custom analytics, exporting data, and the like. APIs are commonly a collection of one or more computing protocols and/or routines that indicate a software program's or software service's functions, and each function's requisite inputs. The APIs may be used to query and fetch data from databases, or pass information to other services or programs. For example, APIs may be used to communicate information and instructions to cloud-based services regarding the meal choices associated with particular micro-fenced locations. APIs may be used to facilitate communications between a plurality of servers underlying web-based or network-based services used by the consumers to monitor, access, or manage meal choices. For example, data supplied from APIs associated with Weight Watchers®, Atkins®, South Beach Diet®, TLC Diet or DASH plan can be available for consumption by the nutrition management server.

Embodiments of the invention present several advantages over existing systems. The foregoing method descriptions and the process flow diagrams are provided merely as illustrative examples and are not intended to require or imply that the steps of the various embodiments must be performed in the order presented. As will be appreciated by one of skill in the art the steps in the foregoing embodiments may be performed in any order. Words such as "then," "next," and "etc.," are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. The invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein. While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method comprising:
   identifying, by a server, a location of an electronic device by receiving a unique beacon identifier from the electronic device, the unique beacon identifier being broadcasted by a beacon device within a plurality of beacons, captured by the electronic device, and transmitted to the server by the electronic device;

upon the electronic device being located within a predetermined boundary, retrieving, by the server, a plurality of meal datasets offered within the predetermined boundary, each meal dataset being associated with a station;

upon displaying, on the electronic device, a map of the boundary having a set of stations corresponding to locations of the plurality of meal datasets in relation to the electronic device, receiving, by the server, a selection of a subset of the plurality of meal datasets, wherein the server displays an indicator for each station displayed on the map where each indicator corresponds to a nutritional attribute of its respective meal dataset in relation to a predetermined nutritional preference; and displaying, by the server, instructions to reach a second location away from the identified location of the electronic device, the second location being associated with at least one station associated with each meal dataset within the subset of the plurality of meal datasets in relation to the location of the electronic device.

2. The method of claim 1, further comprising:
displaying, by the server, nutritional information corresponding to the meal datasets within the subset of the plurality of meal datasets.

3. The method of claim 2, wherein the meal dataset within the subset of the plurality of meal datasets comprises at least one of a calorific content value, ingredients value, macronutrient content value, and micronutrient content value.

4. The method of claim 1, wherein the map is a heatmap comprising a color-coded map indicating at least one selected meal datasets in relation to the location of the electronic device.

5. The method of claim 1, wherein the server outputs instructions in form of a haptic alert.

6. A computer system comprising:
a plurality of beacon devices, each beacon device configured to broadcast a unique beacon identifier;
an electronic device configured to capture the unique beacon identifier from at least one beacon identifier and transmit the unique beacon identifier to a server; and
the server in communication with the electronic device, the server configured to:
identify a location of the electronic device by receiving the unique beacon identifier from the electronic device;
upon the electronic device being located within a predetermined boundary, retrieve a plurality of meal datasets offered within the predetermined boundary, each meal dataset being associated with a station;
upon displaying, on the electronic device, a map of the boundary having a set of stations corresponding to locations of the plurality of meal datasets in relation to the electronic device, receive a selection of a subset of the plurality of meal datasets, wherein the server displays an indicator for each station displayed on the map where each indicator corresponds to a nutritional attribute of its respective meal dataset in relation to a predetermined nutritional preference; and
display instructions to reach a second location away from the identified location of the electronic device, the second location being associated with at least one station associated with each meal dataset within the subset of the plurality of meal datasets in relation to the location of the electronic device.

7. The computer system of claim 6, wherein the server is further configured to:
display nutritional information corresponding to the meal datasets within the subset of the plurality of meal datasets.

8. The computer system of claim 7, wherein the meal dataset within the subset of the plurality of meal datasets comprises at least one of a calorific content value, ingredients value, macronutrient content value, and micronutrient content value.

9. The computer system of claim 6, wherein the server is further configured to output the instructions in form of a map showing one or more physical locations of at least one meal datasets within the subset of meal datasets within the subset of the plurality of meal datasets in relation to the location of the electronic device.

10. The computer system of claim 9, wherein the map is a heatmap comprising a color-coded map indicating at least one selected meal datasets in relation to the location of the electronic device.

11. The computer system of claim 6, wherein the server outputs instructions in form of a haptic alert.

12. An electronic device in communication with a server, the electronic device configured to:
capture at least one unique beacon identifier broadcasted by a beacon device within a plurality of beacons;
transmit to the server by the electronic device, whereby the server:
identifies a location of the electronic device by receiving the unique beacon identifier from the electronic device;
upon the electronic device being located within a predetermined boundary, retrieves a first plurality of meal datasets offered within the predetermined boundary, each meal dataset being associated with a station;
upon displaying, on the electronic device, a map of the boundary having a set of stations corresponding to locations of the plurality of meal datasets in relation to the electronic device, receives a selection of a subset of the plurality of meal datasets, wherein the server displays an indicator for each station displayed on the map where each indicator corresponds to a nutritional attribute of its respective meal dataset in relation to a predetermined nutritional preference; and
displays instructions to reach a second location away from the identified location of the electronic device, the second location being associated with at least one station associated with each meal dataset within the subset of the plurality of meal datasets in relation to the location of the electronic device.

13. The electronic device of claim 12, wherein the electronic device displays nutritional information corresponding to the meal datasets within the subset of the plurality of meal datasets.

14. The electronic device of claim 13, wherein the meal dataset within the subset of the plurality of meal datasets comprises at least one of a calorific content value, ingredients value, macronutrient content value, and micronutrient content value.

15. The electronic device of claim 12, wherein the map is a heatmap comprising a color-coded map indicating at least one selected meal datasets in relation to the location of the electronic device.

16. The electronic device of claim 12, wherein the server outputs instructions in form of a haptic alert.

\* \* \* \* \*